United States Patent
Kroll et al.

(10) Patent No.: US 7,809,439 B2
(45) Date of Patent: Oct. 5, 2010

(54) SPECTRUM-DRIVEN ARRHYTHMIA TREATMENT METHOD

(75) Inventors: Mark W. Kroll, Crystal Bay, MN (US); Peter Boileau, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 421 days.

(21) Appl. No.: 12/111,036

(22) Filed: Apr. 28, 2008

(65) Prior Publication Data

US 2008/0200961 A1 Aug. 21, 2008

Related U.S. Application Data

(62) Division of application No. 11/240,950, filed on Sep. 30, 2005, now Pat. No. 7,386,343.

(51) Int. Cl.
*A61N 1/36* (2006.01)
(52) U.S. Cl. .................... 607/4; 607/5; 607/14
(58) Field of Classification Search ............ 607/4, 607/5, 9, 14
See application file for complete search history.

(56) References Cited

U.S. PATENT DOCUMENTS

| | | | |
|---|---|---|---|
| 4,181,133 A | 1/1980 | Kolenik et al. |
| 4,280,502 A | 7/1981 | Baker, Jr. et al. |
| 4,390,021 A | 6/1983 | Spurrell et al. |
| 4,398,536 A | 8/1983 | Nappholz et al. |
| 4,488,553 A | 12/1984 | Nappholz et al. |
| 4,488,554 A | 12/1984 | Nappholz et al. |
| 4,686,988 A | 8/1987 | Sholder |
| 4,708,142 A | 11/1987 | DeCote, Jr. |
| 4,712,555 A | 12/1987 | Thornander et al. |
| 4,729,376 A | 3/1988 | DeCote, Jr. |
| 4,788,980 A | 12/1988 | Mann et al. |
| 4,809,697 A | 3/1989 | Causey, III et al. |
| 4,830,006 A | 5/1989 | Haluska et al. |
| 4,940,052 A | 7/1990 | Mann et al. |
| 4,944,298 A | 7/1990 | Sholder |
| 4,944,299 A | 7/1990 | Silvian |
| 4,969,467 A | 11/1990 | Callaghan et al. |
| 5,144,947 A | 9/1992 | Wilson |
| 5,292,348 A | 3/1994 | Saumarez et al. |
| 5,330,509 A | 7/1994 | Kroll et al. |
| 5,350,410 A | 9/1994 | Kleks et al. |

(Continued)

OTHER PUBLICATIONS

Sierra, Gilberto PhD et al., "Spectral Analysis of Electrograms During Ventricular Tachycardia in a Canine Model," Journal of Electrocardiology. 1997;30(3):225-237.

(Continued)

*Primary Examiner*—Scott M Getzow
*Assistant Examiner*—Joseph M Dietrich

(57) ABSTRACT

A method and apparatus for treating an arrhythmia is provided. The method includes the steps of: (a) sensing at least one electrical signal from the patient's heart; (b) calculating a frequency spectrum of each electrical signal; (c) calculating a center frequency for each frequency spectrum; and (d) selecting an electro-therapy for delivery to the patient's heart based on the center frequency. The electro-therapy can be a preprogrammed anti-tachycardia pacing (ATP) therapy, a shock therapy, or no therapy at all. The method is performed through the use of an implantable cardioverter defibrillator (ICD). Also provided is a method of determining the optimal location to deliver the electro-therapy.

8 Claims, 4 Drawing Sheets

U.S. PATENT DOCUMENTS

| | | | |
|---|---|---|---|
| 5,365,426 A * | 11/1994 | Siegel et al. | 600/515 |
| 5,683,424 A * | 11/1997 | Brown et al. | 607/5 |
| 6,208,899 B1 * | 3/2001 | Kroll | 607/9 |
| 6,275,734 B1 | 8/2001 | McClure et al. | |
| 6,622,042 B1 * | 9/2003 | Thacker | 607/14 |
| 6,731,982 B1 | 5/2004 | Kroll et al. | |
| 6,754,531 B1 | 6/2004 | Kroll et al. | |
| 6,766,195 B1 | 7/2004 | Bornzin et al. | |
| 6,766,196 B1 | 7/2004 | Kroll et al. | |
| 6,775,572 B2 | 8/2004 | Zhu et al. | |
| 6,795,731 B1 | 9/2004 | Kroll et al. | |
| 6,801,806 B2 | 10/2004 | Sun et al. | |

OTHER PUBLICATIONS

Wathen, Mark S. Md et al., "Prospective Randomized Multicenter Trial of Empirical Antitachycardia Pacing Versus Shocks for Spontaneous Rapid Ventriculqar Tachycardia in Patients With Implantable Cardioverter-Defibrillator," Circulation. 2004;110:2591-2596.

NonFinal Office Action, mailed Sep. 25, 2007: U.S. Appl. No. 11/240,950.

Notice of Allowance, mailed Apr. 4, 2008: U.S. Appl. No. 11/240,950.

* cited by examiner

RV TIP-RING

SPECTRUM $F_c^1$ FREQUENCY ⟶

LV TIP-RING

SPECTRUM $F_c^2$ FREQUENCY ⟶

SPECTRUM-DRIVEN ARRHYTHMIA TREATMENT METHOD

CROSS REFERENCE TO RELATED APPLICATIONS

This application is a division of copending U.S. patent application Ser. No. 11/240,950, filed Sep. 30, 2005, titled "Spectrum-Driven Arrhythmia Treatment Method."

FIELD OF THE INVENTION

The present invention relates generally to implantable cardiac devices. More specifically, the present invention relates to an implantable cardiac device and method of treating arrhythmia.

BACKGROUND OF THE INVENTION

The heart is a series of pumps that are carefully controlled by a very special electrical system. This electrical system attempts to regulate the heart rate between 60 and 100 beats per minute (bpm). Abnormally fast heart rates are called tachycardias. As used herein, the term tachycardia means a heartbeat at a rate which is abnormally high and accordingly considered to be dangerous if permitted to continue, or any arrhythmia involving recognizable heartbeat patterns containing repetitions which are in excess of a periodic heartbeat within a safe range.

When the ventricular chambers beat too quickly, the arrhythmia (i.e., unusual heart rhythm) is known as ventricular tachycardia (VT). When VT occurs, the ventricles may not be able to fill with enough blood to supply the body with the oxygen rich blood that it needs. Symptoms of VT include feeling faint, sometimes passing out, dizziness, or a pounding in the chest.

Ventricular fibrillation (VF) is a very fast and irregular heartbeat that is caused by abnormal impulses coming from several areas of the heart. These abnormal impulses take over the natural pacemaker function of the sinoatrial (SA) node. The heartbeat is so fast that the heart does not have time to pump enough blood to the brain and body tissue, which may cause unconsciousness, cardiac arrest, or death. Ventricular fibrillation has typically been treated using shock therapy. When a patient's heart is found to be in VF, a jolting electrical pulse, or shock pulse, is delivered to the patient in order to reactivate the electrical signals throughout the heart. The shock pulse may be administered via external defibrillators, or via implantable cardioverter defibrillators (ICDs) configured to deliver such a shock. Patients, however, feel uncomfortable using shock therapy because of the pain and discomfort associated with the shock. This is particularly the case if the shock therapy is applied frequently due to the reoccurring nature of VF.

Ventricular tachycardia, on the other hand, may be controlled by medication in some cases. If medications are not effective, the physician may elect to control the rhythm by electrical methods, such as anti-tachycardia pacing (ATP) therapy.

Generally, VT is distinguished from VF by heart rate. For example, if the heart rate is between 150-210 bpm, the condition is generally considered to be a treatable VT, and therefore ATP therapies may be applied. Heart rates higher than 210 bpm are generally considered to be VF, and are immediately treated with shock. Recent studies, however, have found that ATP therapies can successfully treat heart conditions where the heart rate is above 210 bpm, what was once considered the dividing line between treatable VT and VF. If a more effective method of distinguishing between treatable VT and VF is found, patients can be effectively treated with ATP therapies and avoid the uncomfortable pain of shock therapy.

SUMMARY

A method of treating an arrhythmia in a patient's heart is presented. In one embodiment, the method of treating arrhythmia includes: (a) sensing a plurality of electrical signals from a plurality of locations in the heart; (b) calculating a center frequency for each of the plurality of electrical signals; (c) calculating a global median frequency from the center frequencies; (d) selecting an electro-therapy based on the global median frequency; and (e) delivering the electro-therapy to the heart. The electro-therapy can be a pre-programmed anti-tachycardia pacing (ATP) therapy, or a shock therapy.

A method of determining an anti-tachycardia pacing (ATP) sweet spot in a patient's heart is also presented. In one embodiment, the method of determining the ATP sweet spot includes: (a) sensing a plurality of electrical signals from a plurality of electrodes disposed at a plurality of locations with respect to the patient's heart; (b) calculating a frequency spectrum for each of the plurality of electrical signals; (c) calculating a center frequency for each of the frequency spectrums; and (d) defining an ATP sweet spot to be the location where the electrode sensing the electrical signal with the highest center frequency is disposed.

A method of choosing amongst a plurality of electro-therapies for delivery to a patient's heart is also presented. In one embodiment, the method of choosing an electro-therapy includes: (a) sensing an electrical signal from the patient's heart; (b) calculating a frequency spectrum of the electrical signal; (c) calculating a center frequency of the frequency spectrum; and (d) selecting an electro-therapy for delivery to the patient's heart based on the center frequency.

An implantable cardioverter defibrillator (ICD) that delivers an electro-therapy to a patient's heart is also presented. In one embodiment, the ICD includes a sense circuit, a processor, and a therapy circuit. The sense circuit is adapted to receive at least one electrical signal from at least one electrode disposed with respect to the heart. The processor is coupled to the sense circuit and calculates a frequency spectrum of each electrical signal, calculates a center frequency from each frequency spectrum, and calculates a global median frequency from amongst the center frequencies. The therapy circuit is responsive to the processor and is adapted to deliver an electro-therapy to the heart depending on the global median frequency.

In an alternate embodiment, the ICD includes means for sensing electrical signals from the heart, means for calculating frequency spectrums of the electrical signals, means for calculating center frequencies of the frequency spectrums, means for calculating a global median frequency from the center frequencies, and delivery means to deliver an electro-therapy to the heart based on the global median frequency. The ICD further includes means of determining an ATP sweet spot, wherein the delivery means delivers the electro-therapy to the ATP sweet spot.

BRIEF DESCRIPTION OF THE FIGURES

The accompanying drawings, which are incorporated herein, form part of the specification and illustrate the methods and ICD apparatus for delivering electro-therapies to a patient's heart presented herein. Together with the description, the drawings further serve to explain the principles of and to enable a person skilled in the relevant art(s) to make and use the methods and ICD apparatus presented herein. In the drawings, like reference numbers indicate identical or functionally similar elements.

DETAILED DESCRIPTION OF THE INVENTION

The following detailed description of the methods and ICD apparatus for delivery of electro-therapies to a patient's heart refers to the accompanying drawings that illustrate example embodiments. Other embodiments are possible, and modifications may be made to the embodiments within the spirit and scope of the methods and ICD apparatus presented herein. Therefore, the following detailed description is not meant to limit the methods and ICD apparatus presented herein. Rather, their scope is defined by the appended claims.

It would be apparent to one of skill in the art that the methods and ICD apparatus, as described below, may be implemented in many different embodiments of hardware, software, firmware, and/or the entities illustrated in the figures. Any actual software and/or hardware described herein is not limiting of the methods and ICD apparatus presented herein. Thus, the operation and behavior of the methods and ICD apparatus presented will be described with the understanding that modifications and variations of the embodiments are possible, given the level of detail presented herein.

Before describing the example methods in detail, it is helpful to describe an example environment in which they may be implemented. The methods and ICD apparatus presented herein, as described below, are particularly useful in the environment of an implantable cardioverter defibrillator (ICD). An ICD is a medical device that is implanted in a patient to monitor electrical activity of a heart and to deliver appropriate electrical therapy; for example, pacing pulses, cardioverting pulses, or defibrillating (or shock) pulses, as required. The term "implantable cardioverter defibrillator" or simply "ICD" is used herein to refer to any implantable cardiac device known in the art.

Figure 1:
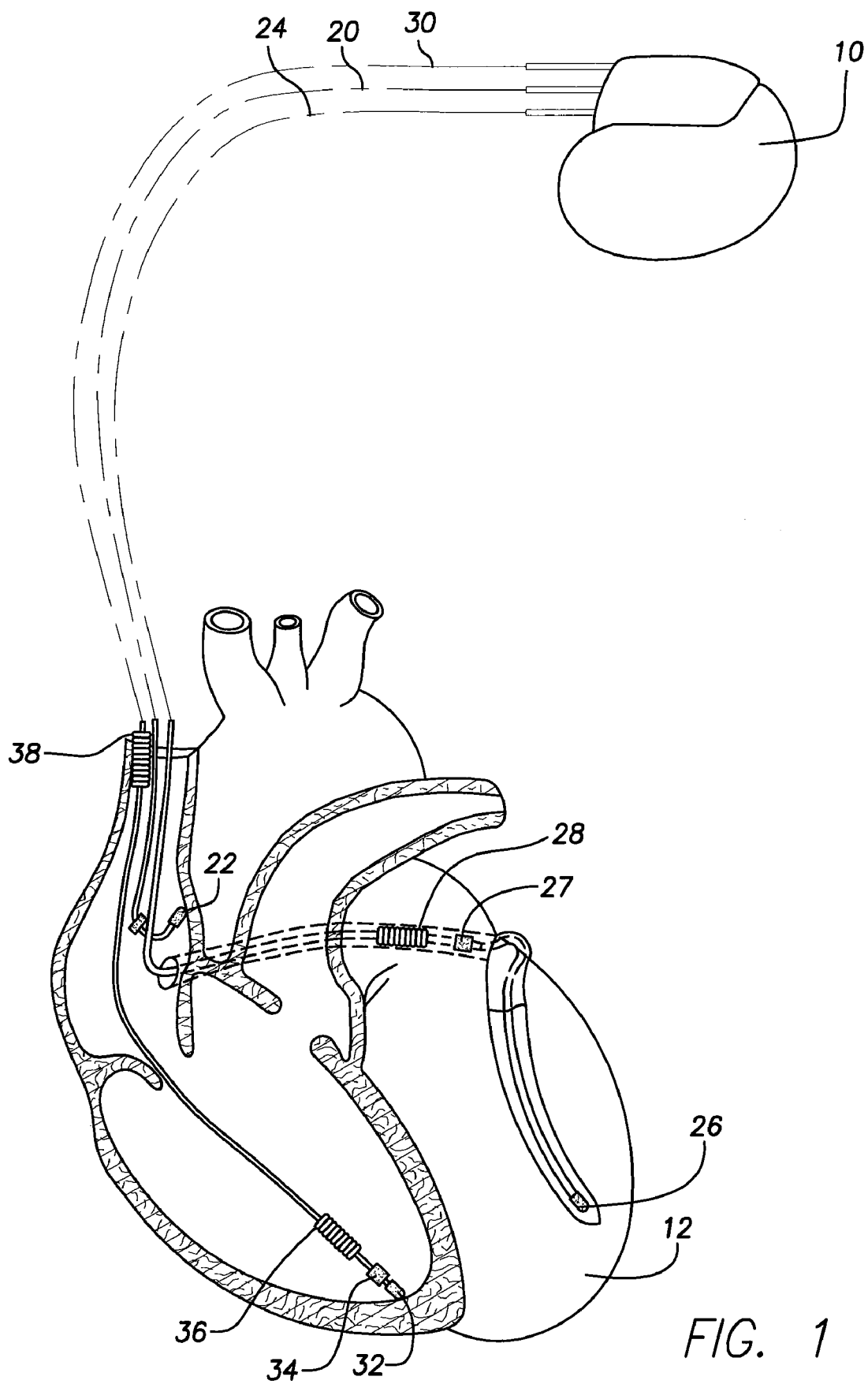
FIG. 1 is a simplified diagram illustrating an exemplary ICD in electrical communication with a patient's heart.

FIG. 1 illustrates an exemplary ICD 10 in electrical communication with a patient's heart 12 by way of three leads 20, 24 and 30, suitable for delivering multi-chamber stimulation and pacing therapy. To sense atrial cardiac signals, and to provide right atrial chamber stimulation therapy, ICD 10 is coupled to implantable right atrial lead 20, having at least an atrial tip electrode 22, which typically is implanted in the patient's right atrial appendage.

To sense left atrial and ventricular cardiac signals, and to provide left-chamber pacing therapy, ICD 10 is coupled to "coronary sinus" lead 24. Lead 24 is designed for placement in the "coronary sinus region," via the coronary sinus, for positioning of a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein, or any other cardiac vein accessible by the coronary sinus. Accordingly, exemplary coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shock therapy using at least a left atrial coil electrode 28.

ICD 10 is also shown in electrical communication with the patient's heart 12 by way of an implantable right ventricular (RV) lead 30 having, in this embodiment, a RV tip electrode 32, a RV ring electrode 34, a RV coil electrode 36, and a superior vena cava (SVC) coil electrode 38. Typically, RV lead 30 is transvenously inserted into heart 12 so as to place the RV tip electrode 32 in the right ventricular apex so that RV coil electrode 36 will be positioned in the RV and SVC coil electrode 38 will be positioned in the SVC. Accordingly, RV lead 30 is capable of receiving cardiac signals and delivering stimulation in the form of pacing and shock therapy to the right ventricle. Other embodiments of ICD 10 may include a single electrode and lead or one or more alternative combinations of the above mentioned electrode and lead configurations.

Amongst other things, any one of, or any combination of, leads 20, 24, and 30, functions as a sense circuit to sense an electrogram (EGM) signal from the heart 12. The EGM signal is then processed within the ICD 10 processor (not shown), as discussed below. The sense circuit, with respective electrodes, and the processor (not shown), thereby serve as means for sensing one or more electrical signals from one or more locations in the patient's heart 12. As will be further discussed below, the processor also serves as a means for calculating one or more frequency spectrums of the electrical signals received from the heart, and means for calculating a plurality of center frequencies of the plurality of frequency spectrums. The processor also serves as a means for selecting one or more electro-therapy for delivery to the heart, from a plurality of therapies, based on the calculations of center frequencies. Further, any one of, or any combination of the leads 20, 24, and 30, in part, function as a therapy circuit to deliver the selected electro-therapy to the heart 12. The therapy circuit, with respective electrodes, and the processor (not shown), thereby serve as means for delivering an electro-therapy to the heart 12.

The selected electro-therapy can be, but is not limited to, anti-tachycardia pacing (ATP) therapy, or shock therapy. If ATP therapy is selected, a pre-programmed series of burst pulses is sent to the heart through any one of, or any combination of, leads 20, 24, and 30. There are several different ATP modalities which have been suggested for termination of tachycardia, with the underlying principle being to stimulate the heart (i.e., using a pacing pulse) at least once shortly after a heartbeat and before the next naturally occurring heartbeat at the rapid rate in an attempt to convert the tachycardia to sinus rhythm. Some examples of patent documents which discuss ATP therapies are U.S. Pat. Nos. 6,731,982; U.S. Pat. No. 4,408,606; U.S. Pat. No. 4,398,536; U.S. Pat. No. 4,488,553; U.S. Pat. No. 4,488,554; U.S. Pat. No. 4,390,021; U.S. Pat. No. 4,181,133; and U.S. Pat. No. 4,280,502, the disclosures of which are hereby incorporated in their entireties by reference.

The most common form of ATP is burst pacing, which delivers a burst of multiple pacing pulses at a cycle length between 50 and 100%, and more typically between 70 and 90%, of the tachycardia cycle length. Delivering pulses having, for example, an 80% cycle length, is also known as delivering pulses having an 80% coupling interval. Each burst of pacing pulses typically includes 2-20 pulses. The number of bursts used is typically 1-15. The rate of each burst can either be a fixed predetermined rate, for example, fixed burst, or a rate that is calculated based on the rate of the arrhythmia being treated, for example, adaptive burst. Acceleration risk is minimized by keeping the number of pulses in a burst, the rate of the burst, and the number of bursts, to the minimum required to terminate the arrhythmia. Many ATP regimens employ variations on this basic theme of burst pacing.

Figure 2:
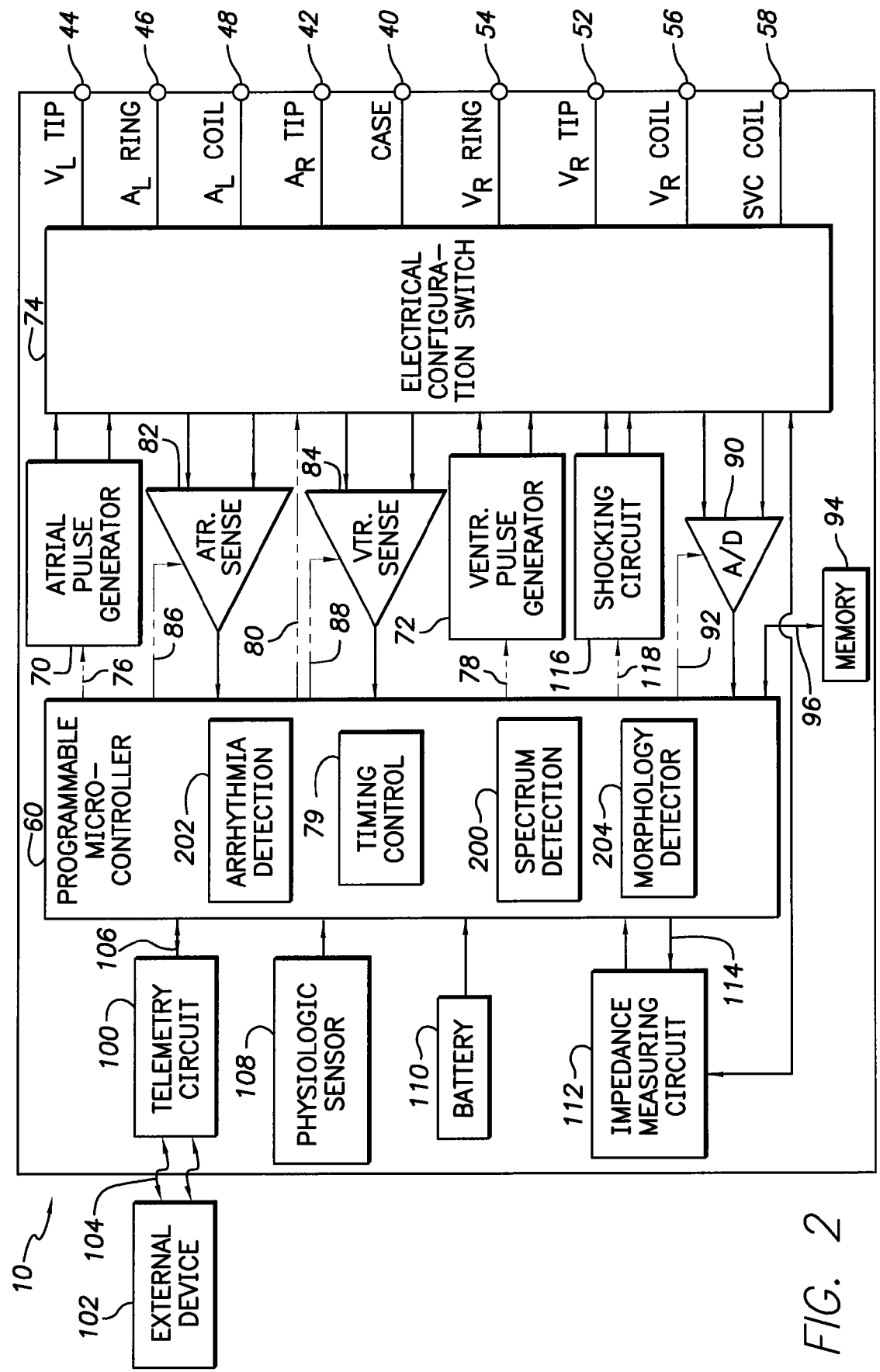
FIG. 2 is a functional block diagram of an exemplary ICD that can provide, amongst other things, cardioversion, defibrillation, and pacing stimulation in three chambers of a heart.

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes 28, 36, and 38, for shocking purposes. Housing 40 further includes a connector (not shown) having a plurality of terminals 42, 44, 46, 48, 52, 54, 56, and 58. These terminals are shown schematically and, for convenience, the names of the electrodes to which they are connected are shown next to the terminals. As such, to achieve right atrial sensing and pacing, the connector includes at least a right atrial tip terminal ($A_R$ TIP) 42 adapted for connection to atrial tip electrode 22.

To achieve left chamber sensing, pacing, and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to left ventricular tip electrode 26, left atrial ring electrode 27, and left atrial coil electrode 28, respectively.

To support right chamber sensing, pacing, and shocking the connector also includes a right ventricular tip terminal ($V_R$ TIP) 52, a right ventricular ring terminal ($V_R$ RING) 54, a right ventricular shocking terminal ($V_R$ COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

At the core of ICD 10 is a programmable microcontroller 60, which controls the various modes of stimulation therapy. As is well known in the art, microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et al.) and the state-machines of U.S. Pat. No. 4,712,555 (Thornander et al.) and U.S. Pat. No. 4,944,298 (Sholder). For a more detailed description of the various timing intervals used within ICDs, and their inter-relationship, see U.S. Pat. No. 4,788,980 (Mann et al.). The '052, '555, '298 and '980 patents are incorporated herein by reference in their entireties.

Microcontroller 60 includes a timing control circuitry 79, which is used to control pacing parameters (e.g., the timing of stimulation pulses, the burst pacing parameters, etc.) as well as to keep track of the timing of refractory periods, post ventricular atrial refractory period intervals, noise detection windows, evoked response windows, alert intervals, marker channel timing, etc., which are well known in the art. Examples of pacing parameters include, but are not limited to, atrio-ventricular delay, interventricular delay, atrial interconduction delay, ventricular interconduction delay, and pacing rate. As will be further discussed below, the timing control circuitry 79, along with arrhythmia detection unit 202 and morphology detection unit 204, serve as means for selecting an appropriate electro-therapy for delivery to the heart, responsive to input from a spectrum detection unit 200. The appropriate therapy can be selected from a plurality of therapies. For example, ATP therapy can be used. Alternative therapies include shock therapy, or any other electro-therapies known in the art.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60, which in turn is able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 84.

For arrhythmia detection, ICD 10 utilizes the atrial and ventricular sensing circuits 82 and 84 to retrieve EGM signals from the heart. The EGM signals are then analyzed in the arrhythmia detection unit 202 of the microcontroller 60. If an arrhythmia is detected, typically based on heart rate, the arrhythmia is then classified by morphology detector unit 204 and analyzed by spectrum detection unit 200, in order to ultimately determine the type of electro-therapy needed (e.g., ATP, bradycardia pacing, cardioversion shocks, burst pacing therapy).

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Advantageously, data acquisition system 90 can be coupled to microcontroller 60, or other detection units, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determine if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated in their entireties herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to heart 12 within each respective tier of therapy. The memory 94 thus serves as means for "learning" which therapies are most effective under certain conditions. As such, when a condition repeats itself, the memory can recognize the condition and adapt the selected therapy to match the previously used successful therapy.

Advantageously, the operating parameters of ICD 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104. For examples of such external devices, see U.S. Pat. No. 4,809,697 (Causey, III et al.); U.S. Pat. No. 4,944,299 (Silvian); and U.S. Pat. No. 6,275,734 (McClure et al.); all patents being hereby incorporated in their entireties herein by reference.

ICD 10 further includes a physiologic sensor 108 that can be used to detect changes in cardiac performance or changes in the physiological condition of the heart. Accordingly, microcontroller 60 can respond by adjusting the various pacing parameters (such as amplitude, rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

ICD 10 further includes a magnet detection circuitry (not shown), coupled to microcontroller 60. The magnet detection circuitry detects when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 is shown as having an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 116 by way of a control signal 118. The shocking circuit 116 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV coil electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 0.5-40 Joules), delivered asynchronously (since R-waves may be too disorganized to be recognized), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 2.

Figure 3A:
FIGS. 3A and 3B show the electrogram signal from the right ventricular tip electrode and corresponding frequency spectrum, respectively.
Figure 3B:
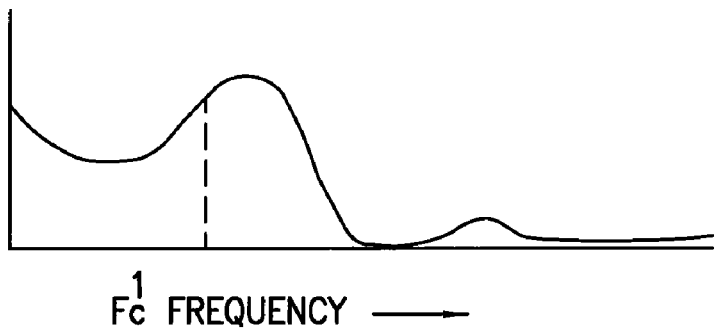

FIG. 3A shows an exemplary EGM signal from the right ventricular (RV) tip electrode 32. The arrhythmia detection unit 202 of the ICD 10 can take such an EGM signal and determine the existence of an arrhythmia based solely on heart rate. Typically, heart rates above 150 bpm will be considered an arrhythmia. After the arrhythmia is detected, the spectral detection unit 200 of the ICD 10 conducts a spectral analysis of the EGM signal. The spectral analysis is conducted using various methods well known in the art, such a Fast Fourier Transform. FIG. 3B shows the frequency spectrum determined from the EGM signal. From the frequency spectrum, a central frequency ($F^1_c$) can be calculated. The $F^1_c$ can be calculated using various mathematical techniques, such as determining the frequency which denotes the half point of the area under the frequency curve of the RV tip electrode 32.

Figure 4A:
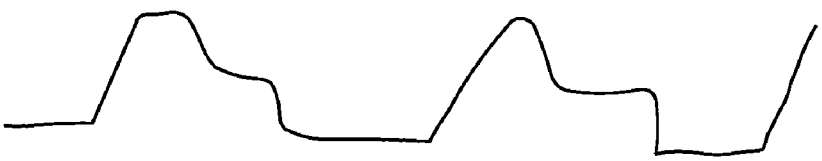
FIGS. 4A and 4B show the electrogram signal from the left ventricular tip electrode and corresponding frequency spectrum, respectively.
Figure 4B:
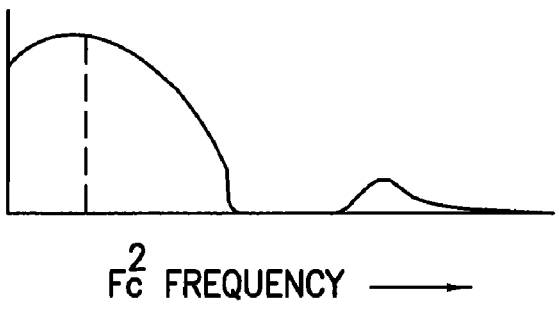

FIG. 4A shows an exemplary EGM signal from the left ventricular (LV) tip electrode 26. FIG. 4B shows the corresponding frequency spectrum of the EGM signal. A second central frequency ($F^2_c$) can be calculated by determining the frequency which denotes the half point of the area under the frequency curve of the LV tip electrode 26. As will be further described below, the ICD 10 can determine whether the detected arrhythmia is a treatable VT based on the spectral analysis of the RV tip EGM signal and the spectral analysis of the LV tip EGM signal.

As shown in FIG. 3A, the RV tip EGM signal has clear and distinct edges. Such a morphology is indicative of the arrhythmia reentrant loop being near the RV tip electrode. In contrast, the LV tip EGM signal shown in FIG. 4A is less defined and the curves are smoother. The frequency spectrum of FIG. 4B shows that there is much more spatial averaging and that the higher frequency components are less pronounced in the LV tip EGM signal than in the RV tip EGM signal. Such a morphology is indicative of the arrhythmia reentrant loop being further away from the LV tip electrode than from the RV tip electrode. Since the RV tip electrode is closer to the arrhythmia reentrant loop, the RV tip EGM signal displays a higher center frequency than the LV tip EGM signal. This distinction is important because an "ATP sweet spot" is defined as the location of the electrode receiving an EGM signal with the highest center frequency. The determination of the location of the ATP sweet spot, in turn, is important because studies have shown that ATP therapies are most effective when delivered to a location nearest to the arrhythmia reentrant loop.

Figure 5:
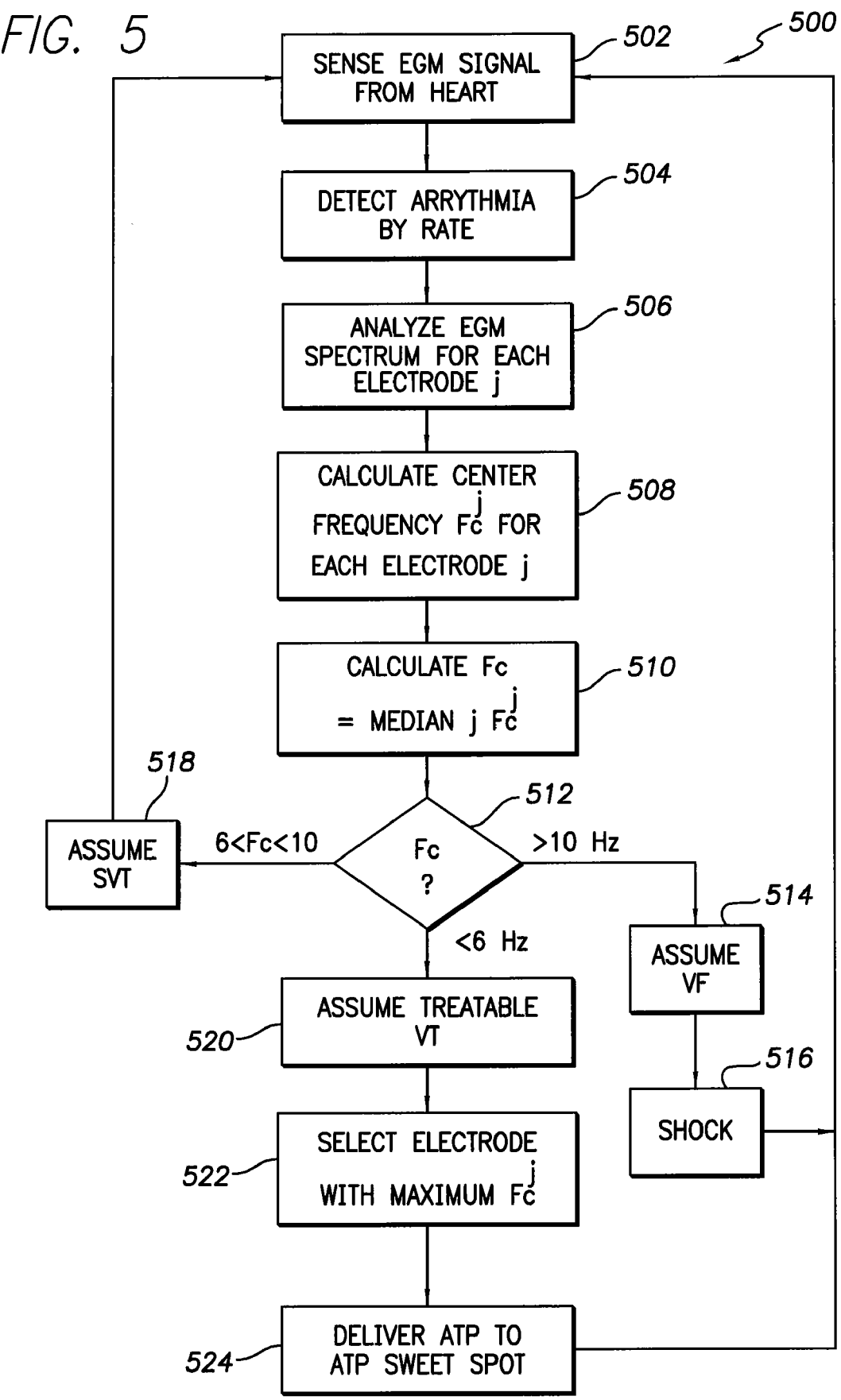
FIG. 5 is a flowchart showing a method of treating arrhythmia.

FIG. 5 is a flowchart showing a method 500 of treating an arrhythmia in accordance with an embodiment. The first step 502 of the method is to sense an EGM signal from the heart using the ICD 10 described above. The EGM signal is preferably sensed by multiple electrodes from multiple locations in the heart. In step 504, the ICD 10 detects the onset of an arrhythmia by heart rate. For example, heart rates above 150 bpm will indicate the onset of an arrhythmia. Arrhythmias detected at heart rates above 150 bpm could be either ventricular tachycardia or ventricular fibrillation.

Generally, VT is distinguished from VF by heart rate. For example, if the heart rate is between 150-210 bpm, the condition is generally considered to be a treatable VT, and therefore ATP therapies are applied. Heart rates higher than 210 bpm are generally considered to be VF, and are immediately treated with shock. Recent studies, however, have found that ATP therapies can successfully treat heart conditions where the heart rate is above 210 bpm, what was once considered the dividing line between treatable VT and VF. The results of one such study were published in "Prospective Randomized Multicenter Trial of Empirical Antitachycardia Pacing Versus Shocks for Spontaneous Rapid Arrhythmia in Patients With Implantable Cardioverter-Defibrillators: Pacing fast arrhythmia reduces shock therapies (painfree rx II) trial results," Wathen et al., *Circulation*, 110(17):2591-6 (Oct. 26, 2004); the entire disclosure of which is hereby incorporated by reference. The method described herein distinguishes treatable VT from VF by spectral analysis, rather than by heart rate.

Once the arrhythmia is detected, the EGM signal for each electrode is analyzed by the spectral detection unit 200 of the ICD 10 in step 506. The spectral detection unit 200 conducts a spectral analysis for each EGM signal received from each electrode (i.e., j electrode from j=1 to j=N, where N is the total number of electrodes). In step 508, the spectral detection unit 200 also calculates a center frequency, as discussed above, for each frequency spectrum of each EGM signal.

In step 510, the global median frequency ($F_C$) is determined. The global median frequency ($F_C$) is calculated by taking the median of the center frequencies ($F_C$=median j($F^j_c$)). A decision-point, shown in step 512, is reached, at which point a therapy decision is made according to $F_C$. If $F_C$ is greater than about 10 Hz, then the processor determines the heart is in VF (step 514), and administers a shock therapy (step 516). After the shock is delivered, the ICD 10 will return to step 502, and continue monitoring for arrhythmia.

If $F_C$ is between about 6 Hz and about 10 Hz, the processor determines the heart is in supraventricular tachycardia (SVT) (step 518), a non-threatening condition, and therefore no electro-therapy will be administered. If the condition of SVT is determined, the ICD 10 will return to step 502, and continue monitoring for arrhythmia.

If $F_C$ is less than about 6 Hz, the processor determines the heart is in a state of treatable VT (step 520). If so, an appropriate ATP therapy shall be selected and delivered to the heart. Before delivering the ATP therapy to the heart, however, the ATP sweet spot is determined by selecting the electrode signaling the highest central frequency (step 522). The ATP therapy is then delivered to the ATP sweet spot through the appropriate electrode (step 524). After delivering the appropriate ATP therapy, the ICD 10 returns to step 502, and continue monitoring for arrhythmia.

In an alternative embodiment, a single EGM signal can be sensed from a single electrode disposed about the heart. If only one EGM signal is detected, step 510 is skipped, and the electro-therapy is selected based on the center frequency. If the center frequency is greater than about 10 Hz, then the processor determines the heart is in VF (step 514), and administers a shock therapy (step 516). If the center frequency is between about 6 Hz and about 10 Hz, the processor determines the heart is in SVT (step 518), and no electro-therapy is administered. If the center frequency is less than about 6 Hz, the processor determines the heart is in a state of treatable VT (step 520), and an appropriate ATP therapy is delivered to the heart (step 524). Since only one EGM signal is sensed, step 522 is skipped and the ATP sweet spot is simply the location of the electrode sensing the EGM signal.

CONCLUSION

Example embodiments of the methods and components of the ICD for delivering electro-therapy to a patient's heart have been described herein. As noted elsewhere, these example embodiments have been described for illustrative purposes only, and are not limiting. Other embodiments are possible and are covered by the methods and ICD apparatus described herein. Such embodiments will be apparent to persons skilled in the relevant art(s) based on the teachings contained herein.

What is claimed is:

1. A method comprising:
   (a) sensing a plurality of electrical signals from a plurality of locations in a heart;
   (b) calculating a center frequency for each of the plurality of electrical signals;
   (c) calculating a global median frequency from the center frequencies; and
   (d) selecting an electro-therapy based on the global median frequency and delivering said electro-therapy using a therapy circuit.

2. A method according to claim 1, wherein step (d) comprises selecting an anti-tachycardia pacing therapy if the global median frequency is less than about 6 Hz, and further comprising:
   (e) delivering the anti-tachycardia pacing therapy to the heart.

3. A method according to claim 1, wherein step (d) comprises selecting a shock therapy if the global median frequency is greater than about 10 Hz, and further comprising:
   (e) delivering the shock therapy to the heart.

4. A method according to claim 1, wherein step (d) comprises selecting no electro-therapy if the global median frequency is between about 6 Hz and about 10 Hz.

5. The method of claim 1 further comprising (e) selecting a location for electro-therapy based on the plurality of center frequencies.

6. A method according to claim 1, wherein step (d) comprises selecting an anti-tachycardia pacing therapy if the global median frequency is less than about 6 Hz, and further comprising:
   (e) calculating a maximum center frequency from the center frequencies;
   (f) defining an ATP sweet spot as the location where the electrical signal having the maximum center frequency is sensed; and
   (g) delivering the anti-tachycardia pacing therapy to the ATP sweet spot.

7. A device comprising:
   a plurality of electrodes adapted to be disposed at a plurality of locations with respect to a patient's heart;
   sensors adapted to sense electrical signals from the plurality of electrodes; and
   a processor programmed to:
     calculate a center frequency for each of the plurality of electrical signals;
     calculate a global median frequency based on the calculated center frequencies; and
     select an electro-therapy based on the global median frequency.

8. A method comprising:
   (a) sensing a plurality of electrical signals from a plurality of electrodes disposed at a plurality of locations with respect to the patient's heart;
   (b) calculating a frequency spectrum for each of the plurality of electrical signals;
   (c) calculating a center frequency for each of the frequency spectrums; and
   (d) calculating a maximum center frequency from the center frequencies; and
   (e) defining a preferred electro-therapy location as the location where the electrical signal having the maximum center frequency is sensed and delivering an electro-therapy to said preferred electro-therapy location using a therapy circuit.

* * * * *